United States Patent [19]

Brennan et al.

[11] Patent Number: 5,403,708
[45] Date of Patent: Apr. 4, 1995

[54] METHODS AND COMPOSITIONS FOR DETERMINING THE SEQUENCE OF NUCLEIC ACIDS

[76] Inventors: Thomas M. Brennan, 2000 Broadway, No. 705, San Francisco, Calif. 94115; Herbert L. Heyneker, 360 Forest Ave., No. 506, Palo Alto, Calif. 94301

[21] Appl. No.: 909,165

[22] Filed: Jul. 6, 1992

[51] Int. Cl.$^6$ .................. C12Q 1/68; C12P 19/34; C07H 21/04
[52] U.S. Cl. ................ 435/6; 435/91.52; 436/94; 536/24.33; 536/25.32
[58] Field of Search ............ 435/6, 91.52; 536/27; 436/94; 935/78

[56] References Cited

U.S. PATENT DOCUMENTS 5,002,867 3/1991 Macevicz .................. 435/6
5,114,839 5/1992 Blocker .................. 435/6

OTHER PUBLICATIONS

Prober et al., *Science* 238, 336–341 (1987).

*Primary Examiner*—Margaret Parr
*Assistant Examiner*—Kenneth R. Horlick
*Attorney, Agent, or Firm*—Richard F. Trecartin

[57] ABSTRACT

Methods and compositions for forming ligation product hybridized to a nucleic acid template. The ligation product is formed by contacting a nucleic acid template with a primer capable of hybridizing to the template to form a primed template. The primed template is then contacted with a pool of random extension oligonucleotides of length N and an enzyme system. The enzyme system is capable of covalently linking the primer to an extension oligonucleotide adjacently hybridized to it and one or more other extension oligonucleotides adjacently hybridized to the ligation product defined by covalently linked ligation primer and one or more extension oligonucleotides. When covalently linked, the ligation product is hybridized to the nucleic acid template. Modifications permit the determination of the nucleotide sequence of one or more members of a first set of target nucleotide residues in the nucleic acid template that are spaced at intervals of N nucleotides. In such sequencing methods, labeled ligation product is formed wherein the position and type of label incorporated into the labeled ligation product provides information concerning the nucleotide residue in the nucleic acid template with which the labeled nucleotide residue is base paired. The compositions comprise a pool of oligonucleotides of a predetermined length N containing at least one differentially labeled sequencing nucleotide residue at a predetermined position and random nucleotide residues at each of the other nucleotide positions.

13 Claims, 6 Drawing Sheets

|  | 1ST REACTION PRODUCT | 2ND REACTION PRODUCT | 3RD REACTION PRODUCT |
|---|---|---|---|
| 15 bp | — A* = T | — T* = A | — A* = T |
| 12 bp | — A* = T | — C* = G | — G* = C |
| 9 bp  | — G* = C | — T* = A | — T* = A |
| 6 bp  | — T* = A | — A* = T | — C* = G |

METHODS AND COMPOSITIONS FOR DETERMINING THE SEQUENCE OF NUCLEIC ACIDS

FIELD OF THE INVENTION

The invention relates to improved methods and compositions for determining the sequence of nucleic acids.

BACKGROUND OF THE INVENTION

The basic techniques for sequencing DNA include the Maxam-Gilbert chemical-degradation method (Maxam, A. M. and Gilbert, W. (1977) *Proc. Natl. Acad. Sci. U.S.A.* 74:560) and the dideoxy termination method of Sanger (Sanger, et al. (1977) *Proc. Natl. Acad. Sci. U.S.A.* 74:5463-5467). In addition, improvements have been made in conventional electrophoretic and capillary gel-based sequencing methods and various proposals have been made to use multiplexed vectors (Church, et al. (1988) *Science* 240:185), fluorescent single molecule exonuclease digestion (Keller, et al. (1989) *J. Bio. Molecular Structure and Dynamics* 7:301), scanning tunneling microscopy (Beebe, et al. (1989) *Science* 243:370), laser X-ray diffraction (*Human Geno News* 2, No. 2, paged 4 (1990)), laser deadsorption mass spectrometry (Williams, et al. (1989) *Science* 246:1585), sequencing by hybridization (Khrapko, et al. (1989) *FEBS Letters* 256:118; Bains, et al. (1988) *J. Theoro. Biol.* 135:303; and Drmanac, et al. (1988) *Genomics* 4:114), array determination of DNA sequence by mass spectrometry (U.S. Pat. No. 5,003,059), as well as suggestions to use isotopic sulfur (Brennan, et al., *Biological Mass Spectrometry*, page 159, Editor A. L. Burlingame, Elsevier (New York 1990)), or metals (Jacobson, et al. (1991) *Anal. Chem.* 63:402) and chemiluminescent detection systems (Bronstein, et al. (1990) *BioTechniques* 8:310). However, none of the foregoing methodologies provide a comprehensive solution to the problem of large scale sequence analysis of genomes such as that of the human species.

In conventional nucleotide hybridization sequencing, the length of DNA which can be unambiguously reconstructed from a set of all complementary oligonucleotides with one-base offset is limited by the occurrence of repeating patterns of sub-sequence. With 8-mer probes, the average length of fragment which can be reconstructed unambiguously is about 185 bp (Drmanac, et al. (1989) *Genomics* 4:114).

Recently, it was proposed that hexamers could be used in sequential primer elongation by ligation (SPEL) as a method to construct specific members of the 12-, 18- and 24-mer library as walking primers (Szybalski (1990) *Gene* 90:177).

Finally, an oligonucleotide ligation assay (OLA) has been described for detecting point mutations wherein differentially labeled oligonucleotides that hybridge adjacent to each other in the proper orientation to a target sequence they can be covalently linked with T4 ligase (Landergn, et al. (1988) *Science* 241:1077 and U.S. Pat. No. 4,988,617).

Each of the foregoing sequencing methodologies has inherent limitations. For example, the laser X-ray diffraction, laser desorption and mass spectrometry methods require the use of expensive and sensitive instruments. The fluorescent single molecule exonuclease digestion method (also referred to as the Los Alamos approach) requires labeling at all nucleotide positions with a fluorescent dye to specifically identify that base. Yet, it has proved very difficult to induce the known DNA polymerases to incorporate multiple base specific fluorescent labels. A significant limitation in the Sanger or Maxam-Gilbert sequencing protocols is the length of DNA which can be sequenced. This length is limited experimentally by the ability to electrophoretically resolve labeled fragments differing in length from each other only by one nucleotide base. Although there have been reports of occasional read lengths in excess of 1,000 bp on long thin gels (Slighton, et al. (1991) *Anal. Biochem.* 192:441), the average practical limit is about 500-600 bp (Nishakawa, et al. (1991) *Electrophoresis* 12:623).

Given the foregoing limitations, it is apparent that simple and cost-effective methods are needed to determine the sequence of nucleic acids. Accordingly, it is an object herein to provide methods and compositions that provide information relating to the sequence or a subsequence of a nucleic acid spanning >1 kb. Such methods and compositions are cost-effective and readily adapted to automation.

SUMMARY OF THE INVENTION

The invention includes methods for forming ligation product hybridized to a nucleic acid template. The ligation product is formed by contacting a nucleic acid template with a primer P capable of hybridizing to the template to form a primed template. The primed template is then contacted with a pool of random extension oligonucleotides of length N and an enzyme system. The enzyme system is capable of covalently linking the primer to an extension oligonucleotide adjacently hybridized to it and one or more other extension oligonucleotides adjacently hybridized to the ligation product defined by covalently linked ligation primer and one or more extension oligonucleotides. When covalently linked, the ligation product is hybridized to the nucleic acid template.

The invention also includes modifications of the foregoing method that permit the determination of the nucleotide sequence of one or more members of a first set of target nucleotide residues in the nucleic acid template that are spaced at intervals of N nucleotides. In such sequencing methods, labeled ligation product is formed wherein the position and type of label incorporated into the labeled ligation product provides information concerning the nucleotide residue in the nucleic acid template with which the labeled nucleotide residue (sequencing nucleotide residue) is base paired. In some aspects of the invention, only one labeled nucleotide residue is incorporated into each molecule of a ligation product formed. In such cases, however, the labeled ligation product comprises a heterogenous population comprising ligation products having different lengths which differ by N nucleotide residues or a multiple thereof. The detection of the relative position and the type of label in the sequence nucleotide residue in the heterogenous ligation product is generally determined by size separating the ligation product coupled with detection of the type of label incorporated in each ligation product of a specific size.

In other aspects of the invention, the labeled ligation product contains more than one labeled nucleotide residue. In such cases, the labeled nucleotide residues are positioned in the ligation product at an interval of N nucleotides or a multiple thereof. The determination of the relative position and the type of label for the sequencing nucleotide residues in such a ligation product is generally determined by use of an exonuclease coupled with a detector appropriate for the label used.

The invention also includes compositions useful in practicing the methods of the invention. The compositions comprise a pool of oligonucleotides of a predetermined length N containing at least one differentially labeled sequencing nucleotide residue at a predetermined position and random nucleotide residues at each of the other nucleotide positions. The pool of oligonucleotides may also contain four different nucleotides at the predetermined position each of which contain a different nucleotide specific label. The compositions of the invention also include the foregoing compositions further comprising a terminus containing a chain-terminating nucleotide residue incapable of participating in enzyme-mediated ligation.

DETAILED DESCRIPTION OF THE PREFERRED EMBODIMENTS

In its broadest aspect, the invention is directed to methods and compositions for producing a ligation product hybridized to a template nucleic acid. Although specific embodiments of the invention are directed to utilizing this generic method in conjunction with labeled nucleotide residues for the purpose of sequencing nucleic acids, the generic method of producing ligation product is itself useful to generate double stranded nucleic acid from a single stranded nucleic acid template. Further, when used in conjunction with a terminating moiety, the ligation product so formed can be separated from the nucleic acid template on which it is formed and used as size markers used in conjunction with, for example, electrophoretic separation of nucleic acids. Such size markers are advantageous in that they provide size markers differing in a predetermined number of nucleotide residues and as such, cover more of a size continuum as compared to size marker systems commonly used. In practicing this aspect of the invention, the following aspects of the invention relating to the sequencing of nucleic acids applies except that there is no requirement for use of labeled nucleotide residues. Of course, labeled nucleotides can be incorporated into the ligation product. However, when such labeled nucleotide residues are so used, they need not be incorporated in the predetermined nucleotide positions as discussed hereinafter with regard to the sequencing of a nucleic acid template.

A major aspect of the invention relates to methods and compositions for the determination of the nucleotide sequence of nucleic acids. In general, the nucleotide sequence is determined from a predetermined location within the nucleic acid template and can be determined in either the 5' or 3' direction over a nucleotide length that far exceeds that previously obtained using classical sequencing by the Sanger dideoxy or Maxam-Gilbert sequencing methods. In one embodiment of the invention, a partial copy of the nucleic acid template is made in much the same way as in the Sanger dideoxy sequencing method. However, instead of stepping one base at a time using deoxynucleotide triphosphates (dNTPs) and DNA polymerase, primary extension is achieved with a set of random oligonucleotides having a length of N-nucleotide residues and ligase. The ligation product grows in steps of N-nucleotides. Chain termination occurs upon incorporation of a termination moiety.

Figure 1A:
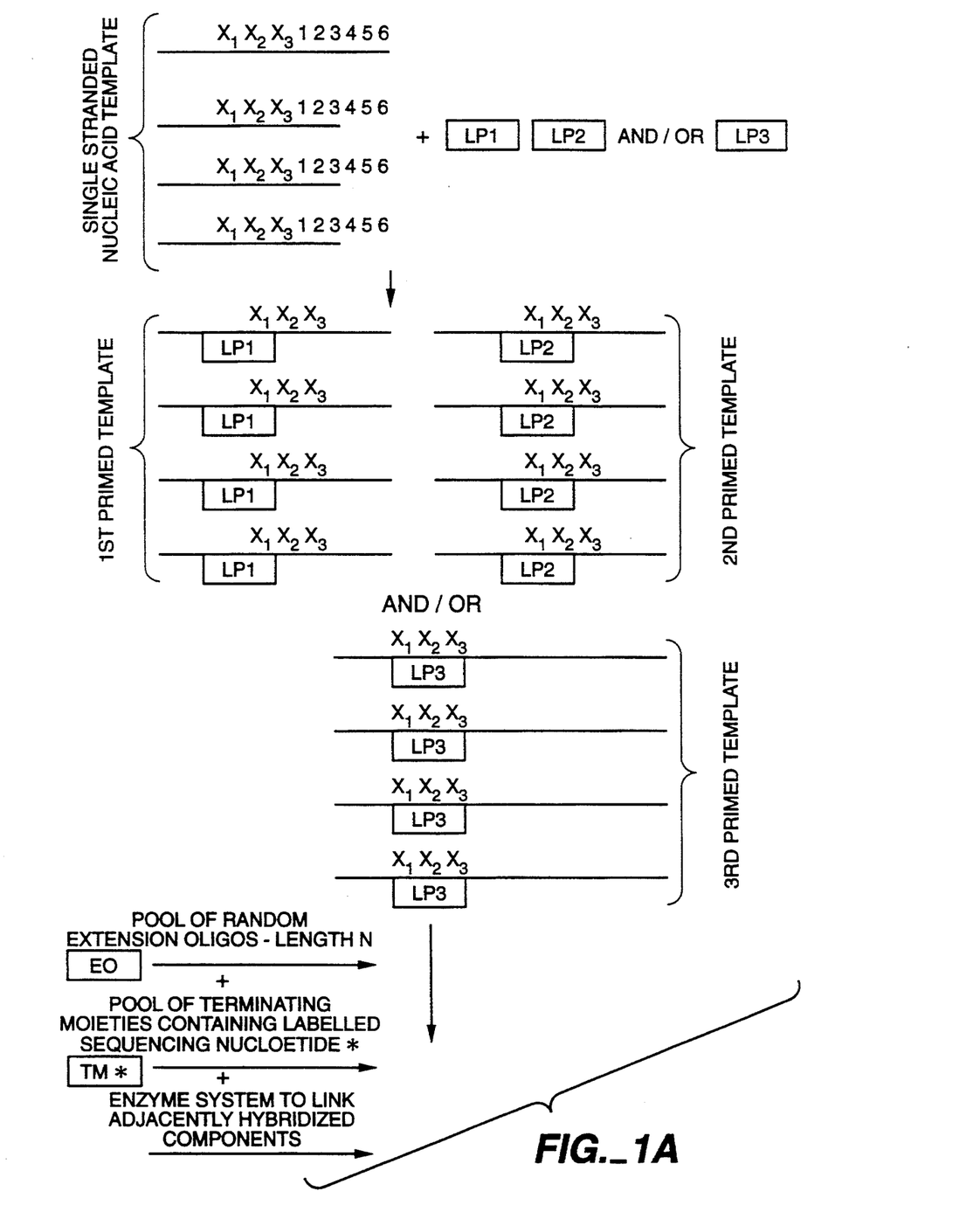
FIGS. 1A and 1B comprise a flow chart depicting the components and method of one embodiment of the invention.
Figure 1B:
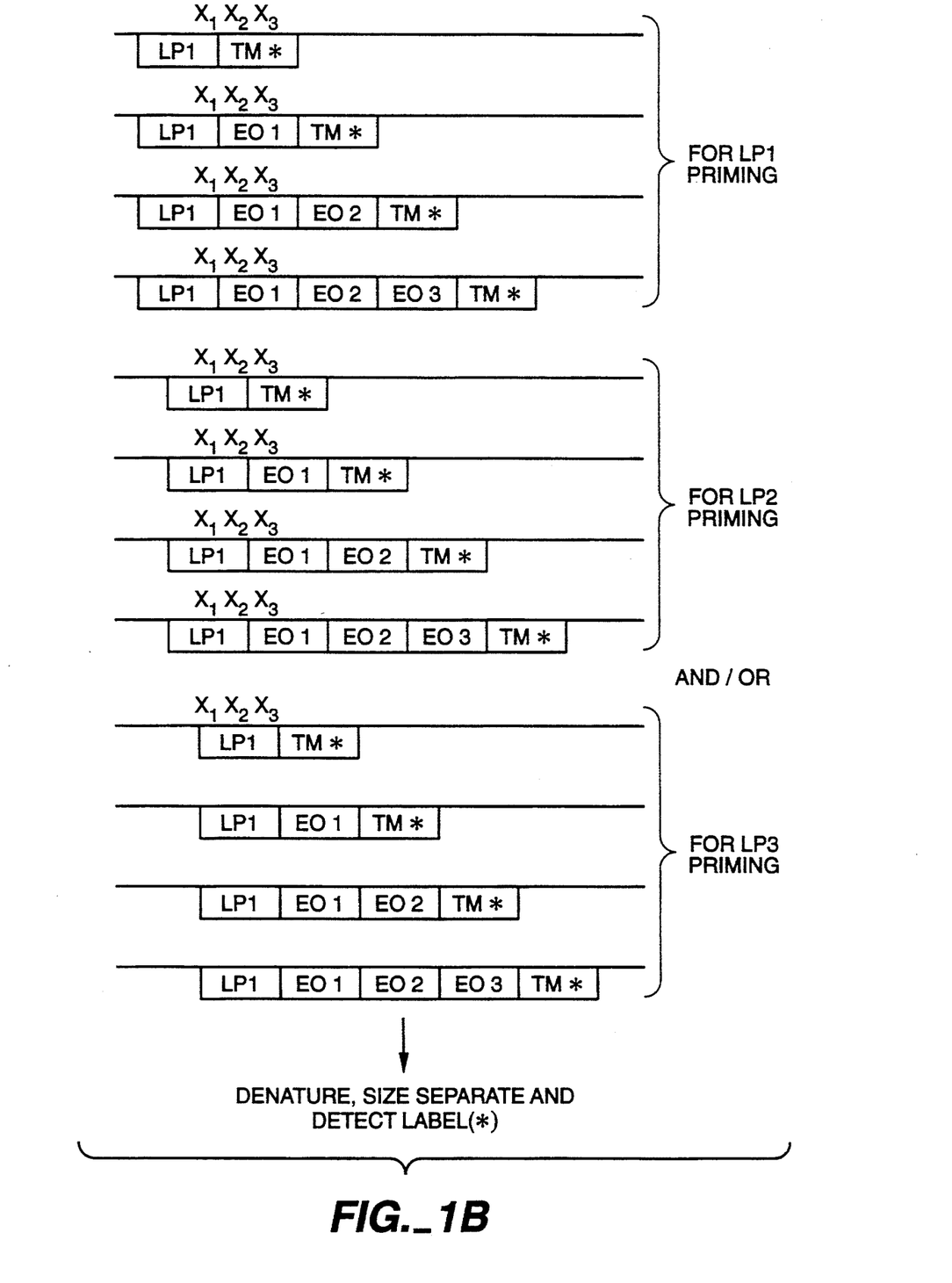

This particular embodiment of the invention as well as other embodiments are more readily understood by reference to the accompanying drawings. Referring now to FIGS. 1A and 1B, the components and method of this embodiment are shown for determining the sequence of a nucleic acid. As indicated in FIG. 1A, single stranded nucleic acid template is contacted with ligation of primers LP1, LP2 and/or LP3. Although various modifications can be made to the specific embodiment disclosed in FIG. 1 which permit the simultaneous use of ligation primers in a single reaction mixture, for the sake of simplicity, each of the ligation primers is added to a separate sample of single stranded nucleic acid template. The sequence of each of the ligation primers and the conditions under which these two components are exposed is such that the ligation primer hybridizes to the single stranded nucleic acid template to form first, second and third primed templates, respectively, for LP1, LP2 and LP3. As indicated, a terminal nucleotide in LP1 is base paired with adjacent nucleotide residue X1 in the single stranded nucleic acid whereas a terminal nucleotide residue in LP2 and LP3 are base paired with nucleotide residues X2 and X3, respectively, in the single stranded nucleic acid template.

Although the ligation primers in FIG. 1 are shown schematically has having a length of only three nucleotides, in practice, the length of the ligation primers is substantially longer to provide sufficient specificity such that the ligation primer hybridizes with one of its terminal nucleotide residue base paired with the nucleotide residues X1, X2 or X3. The length of the ligation primers is preferably chosen such that the primed templates formed upon hybridization are stable under the conditions employed throughout the subsequent steps required for the formation of ligation product. In addition, the different ligation primers need not be of the same length. Thus, for example, LP2 can comprise LP1 with the addition of a nucleotide residue complementary to X2 and LP3 can comprise LP1 with the addition of nucleotide residues complementary to X2 and X3. All that is required is that the terminal nucleotide residue in each of the different ligation primers be capable of base pairing with specific nucleotide residues in the single stranded nucleic acid template that have a known relationship to each other such that they each define a known origin for each sequencing reaction.

When sequencing in the direction defined by one of the ends of the different ligation primers, generally the other end is blocked such that it cannot participate in a ligase-mediated reaction. For example, when a ligation product is being formed in a 5' to 3' direction (i.e., in the 3' to 5' direction on the single stranded nucleic acid template), the 5' end of the ligation primer is blocked, for example, by using a 5' dideoxy terminal nucleotide residue. When sequencing in the other direction, the terminal nucleotide residue of the ligation primer can be a 3' dideoxy nucleotide. Alternatively, the end of the ligation primer not participating in ligation product formation can be attached to one of the members of a binding pair to facilitate subsequent purification of the ligation product formed. Thus, the ligation primer can be attached to streptavidin or avidin or to an antigen or antibody or other member of a receptor-ligand binding pair. The other member of the binding pair can then be used to separate ligation product from other components of the reaction mixture, especially those components containing labeled nucleotide residues not incorporated into the ligation product, to facilitate subsequent detection of the labeled nucleotide residues incorporated into the ligation product.

The primed nucleic acid template is contacted with a pool of random extension oligonucleotides. The random extension oligonucleotides have a predetermined length of N-nucleotide residues and are characterized by a population of $4^N$ oligonucleotides such that all possible sequence combinations of the four different nucleotide residues that are normally present in a nucleic acid are represented. In this particular embodiment, the extension oligonucleotides are not labeled. However, as indicated in an alternate embodiment such extension oligonucleotides can contain a differentially labeled sequencing nucleotide residue at a predetermined position to provide sequencing information.

The length of the extension oligonucleotide is critical to the invention. In FIG. 1, the extension oligonucleotides have a length of 3 nucleotide residues. However, the choice of three nucleotide residues is only for the sake of convenience in describing the invention. Such extension oligonucleotides may be of any length but are preferably from between 2 nucleotides to about 12 nucleotide residues, most preferably between 4 and 9 nucleotide residues. As will become apparent upon further explanation of the invention, the length of the extension oligonucleotides provides a rough measure of the number or nucleotide residues that can be sequenced from the site of ligation primer hybridization. For example, if the maximum number of nucleotide residues which can be read from a Sanger dideoxy sequencing gel is approximately 500 base pairs, the number of base pairs which can be read from the same DNA sequence using the methods and compositions of the invention wherein the extension oligonucleotide has a length of 6 nucleotide residues is approximately $6 \times 500$ base pairs or approximately 3 kb. Similarly, the use of extension oligonucleotides having a length of 8 nucleotide residues permits the sequences of $8 \times 500$ base pair or approximately 4 kb.

The methods used to make the extension oligonucleotides of the invention are well known to those skilled in the art and in general involve solid state synthesis. For each round of nucleotide addition, all four nucleotide residues are utilized until the length of the extension oligonucleotide is produced. A particularly preferred method for synthesizing extension oligonucleotides is that described by *Oligonucleotides and Their Analogs: A Practical Approach*, F. Eckstein, ed., IRL Press (Oxford, U.K. 1991). The extension oligonucleotides can be any type of nucleic acids including DNA or RNA. In some aspects of the invention, oligonucleotides containing altered ribose-phosphate backbones can be used such as oligonucleotides containing phosphorothioate or phosphordithioate linkages which are capable of resisting nuclease digestion.

In addition to the extension oligonucleotides, the primed templates are also contacted with a pool of terminating moieties. In one aspect of the invention, the terminating moieties comprise a terminal nucleotide residue capable of terminating the elongation of the ligation product when covalently incorporated into the ligation product by an enzyme system, e.g., a ligase. In another aspect of the invention, the terminating moiety also comprises at least one labeled nucleotide residue at a predetermined nucleotide position containing a nucleotide-specific label, i.e., a label which identifies the specific nucleotide residue labeled. The labeled nucleotide residue in the terminating moiety is sometimes referred to as the sequencing nucleotide residue. In some aspects, the predetermined nucleotide position in the terminating moiety contains four different nucleotide residues, each of which contains a different nucleotide-specific label.

Figure 4:
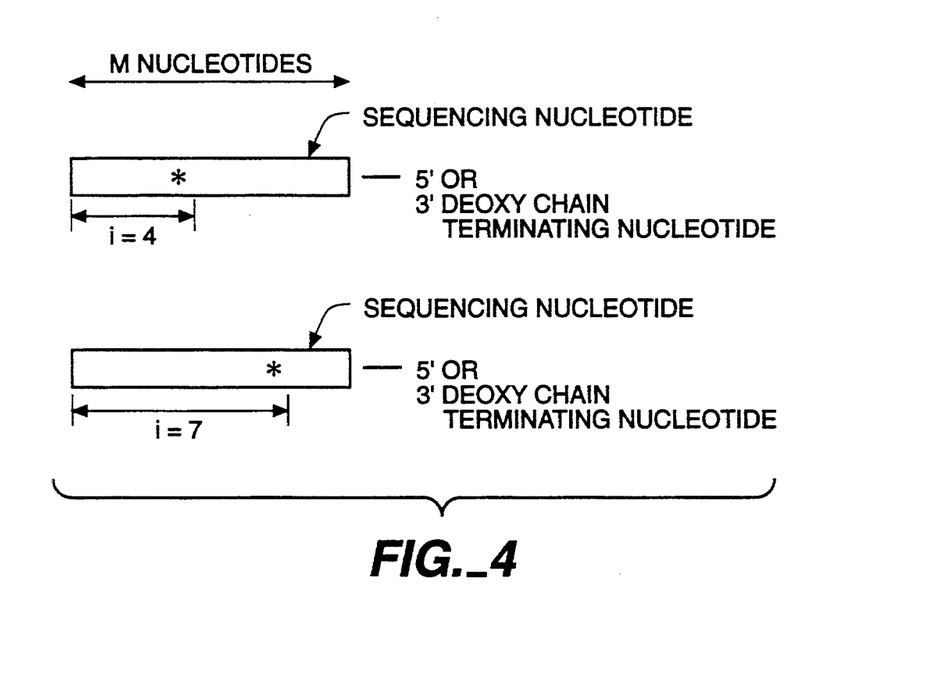
FIG. 4 depicts a terminating moiety comprising an oligonucleotide containing a labeled nucleotide residue (sequencing nucleotide) at a predetermined position and a terminal nucleotide residue capable of terminating elongation. The labeled sequencing nucleotide residue is identified by a (*) and its nucleotide position (i) is defined relative to the terminus of the sequencing oligonucleotide opposite the 5' or 3' terminating nucleotide residue.

FIG. 4 depicts the structure of a chain terminating moiety comprising an oligonucleotide. As can be seen, such oligonucleotides have M-nucleotide residues and either a 3' or 5' terminus which is incapable of being covalently linked to an oligonucleotide. Generally, a 5' or 3' dideoxy nucleotide is used during oligonucleotide synthesis to produce the desired chain-terminating oligonucleotide. Of course, the chain-terminating end of the sequencing oligonucleotide is chosen such that the oligonucleotide is capable of being covalently linked to the ligation product.

Located within the chain-terminating oligonucleotide (also sometimes referred to as a sequencing oligonucleotide) is one or more predetermined nucleotide positions. Each predetermined position contains each of the four different nucleotide residues and a different label for each different nucleotide at that position. The predetermined position of the sequencing nucleotide is defined by its position from the terminus of the sequencing oligonucleotide opposite the chain-terminating end. Thus, in FIG. 4 the upper chain-terminating sequencing oligonucleotide contains a sequencing nucleotide residue at a predetermined nucleotide position 4 whereas the bottom chain-terminating oligonucleotide contains a sequencing nucleotide residue at position 7. In the particular embodiment disclosed in FIG. 1, the position of the sequencing nucleotide residue is held constant in each of the different reaction products while the position of the ligation primers LP1, LP2 and LP3 is varied vis-a-vis the nucleotide residues X1, X2 and X3 with which the terminal nucleotide of each of the ligation primers is base paired. However, as will be apparent once the invention is understood, the ligation primer can be held constant while the position of the sequencing nucleotide residue is sequentially varied in the sequencing oligonucleotide. In such a situation, the same amount of sequence information is derived although the sequence information may be shifted by one or more nucleotides as between the two approaches.

The extension oligonucleotides and terminating moieties are contacted with the primed templates under relatively stringent hybridization conditions such that hybridization is sequence specific, especially for the terminating moiety. Such conditions, of course, depend upon the length of the extension oligonucleotide and terminating moiety and are readily ascertainable by one skilled in the art. However, the hybridization conditions must be chosen such that the enzyme system employed for covalently linking the various components hybridized to the template nucleic acid is not adversely affected. Thus, the type and concentration of salts employed and the temperature of the reaction mixture can be varied to maximize the specificity of hybridization and efficiency of covalent linking by the enzyme system.

In this regard, an enzyme system is also included which is capable of covalently linking the various components that are adjacently hybridized to the primed template.

In general, the enzyme system comprises a single enzyme capable of linking the adjacently hybridized components, e.g., a ligase such as T4 ligase. Other ligases capable of maintaining activity at elevated temperatures can also be used to provide for increasing hybridization stringency at elevated temperatures.

Referring now to FIG. 1B, it can be seen that for each set of reaction products primed by LP1, LP2 or LP3 that a plurality of linked ligation products are formed. In FIG. 1B, each of the reaction products as shown depicts four different ligation products each differing by the number of extension oligonucleotides incorporated into the linked ligation product. For each of the labeled ligation products, it should be noted that the differentially labeled sequencing nucleotide residue designated with an asterisk is base paired with a different nucleotide in the nucleic acid template. The relationship amongst the various linked ligation products in each of the first, second and third reaction products is summarized in FIG. 2. As can be seen, the first reaction product contains labeled sequencing nucleotide residues base paired with nucleotide residues in the nucleic acid template having an interval of N-nucleotides. Such nucleotides define a first reading frame F1 and the nucleotide residues in the nucleic acid template base-paired with the sequencing nucleotide residues are referred to as members of a first set of target nucleotides.

Figure 2:
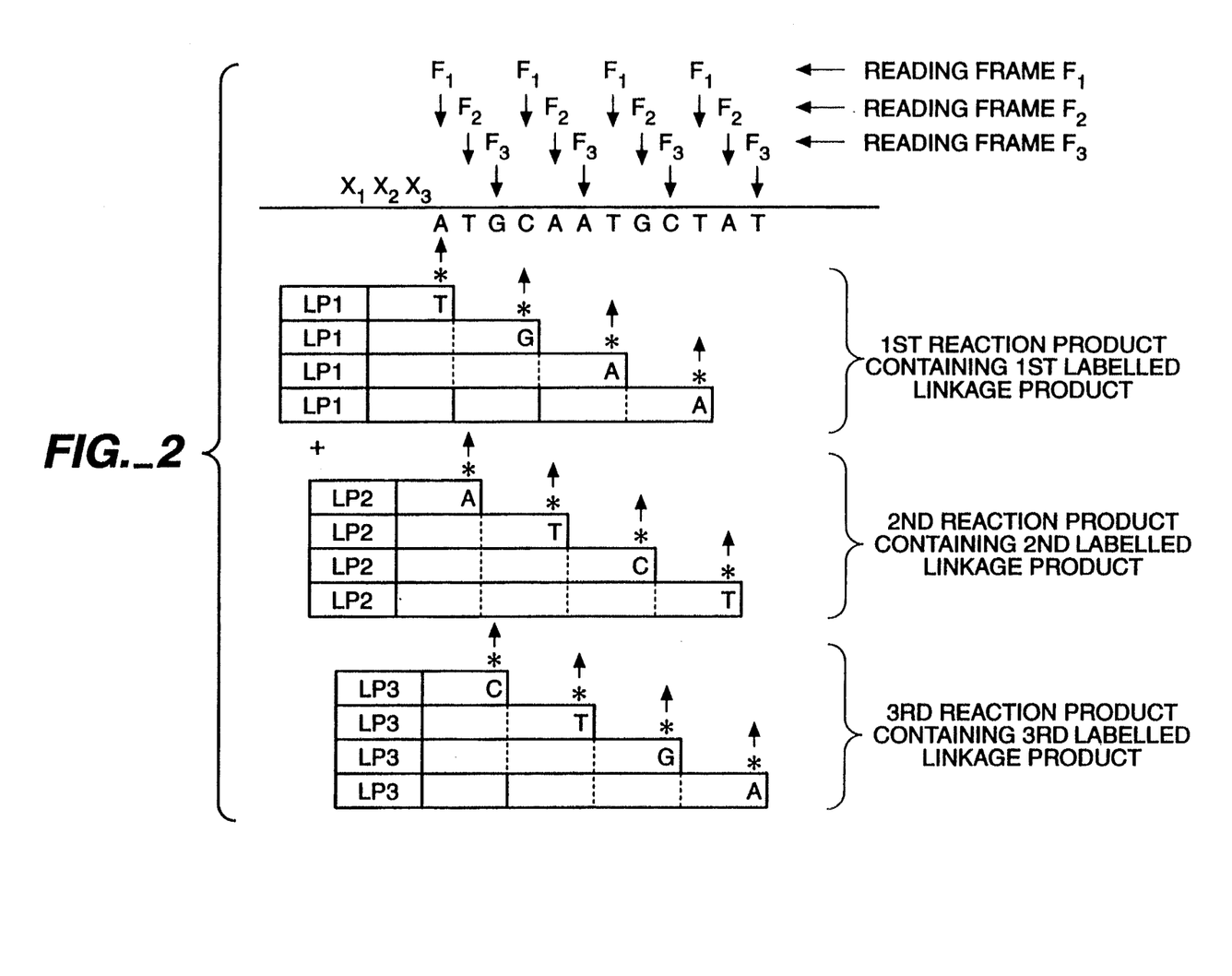
FIG. 2 depicts the relationship of the various ligation products obtained according to the method depicted in FIGS. 1A and 1B. In this figure, a DNA sequence is represented by the standard single letter abbreviations. The sequence reading frames F1, F2 and F3 are shown for this particular sequence based upon the labeled linkage product formed in first, second and third reaction products.

Similarly, the labeled sequencing nucleotide residues in each of the ligation products in the second and third reaction products are base paired, respectively, with nucleotide residues defining second and third reading frames F2 and F3 which define second and third target nucleotide residues in the nucleic acid template. In FIG. 2, an arbitrary DNA sequence spanning 12 adjacent nucleotide residues is set forth together with the differentially labeled sequencing nucleotide residues located in each of the linked ligation products.

When the linked ligation product is separated from the nucleic acid template such as by denaturation, the individual ligation products in each reaction product can be size separated from each other, typically in an electrophoretic medium. The labels associated with each ligation product form can then be determined as an indication of the nucleotide residue present in a particular position in the template nucleic acid which had been base paired with the differentially labeled sequencing nucleotide residue. It is to be understood, of course, that the depiction of only 12 adjacent nucleotides for sequencing in FIG. 2 is for example only. As previously indicated, an extension oligonucleotide of 3 nucleotides should provide the ability to sequence approximately 1,500 nucleotides.

Figure 3:
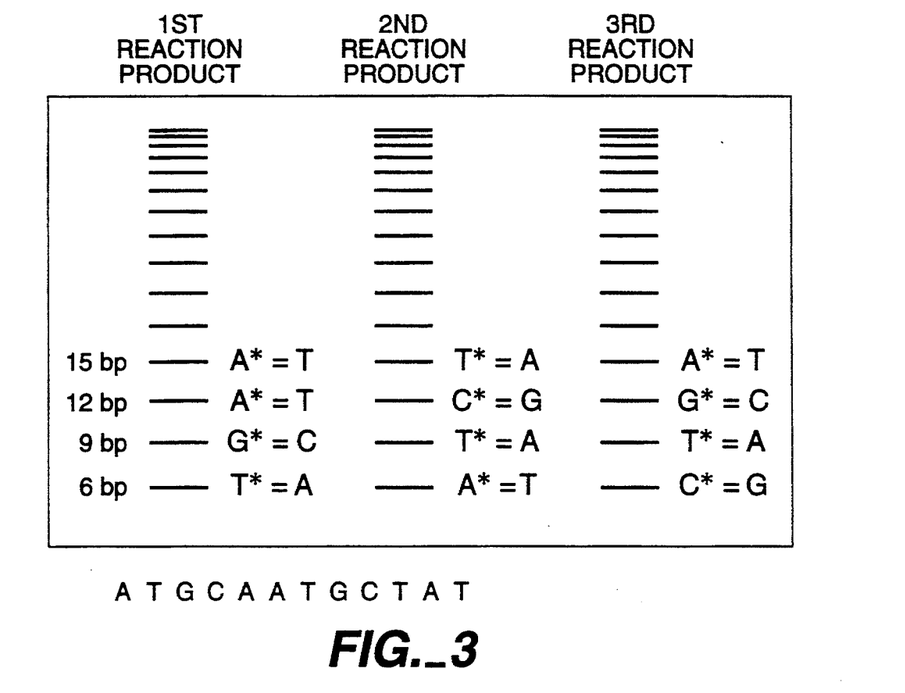
FIG. 3 depicts the electrophoretic separation of the first, second and third reaction products. The labeled sequencing nucleotide residue is identified in each band and the corresponding complementary nucleotide residue present in the nucleic acid template. The nucleotide residue identified in the first, second and third reaction products correspond to those contained within the sequence reading frames F1, F2 and F3, respectively.

FIG. 3 represents one means for size separating the various reaction products of the invention. In FIG. 3, each of the separate reaction products primed by ligation primers LP1, LP2 and LP3 are electrophoretically and simultaneously separated in the same electrophoretic media. Each of the labeled nucleotide residues and its corresponding complementary nucleotide are set forth for the four lowest bands in each of the electrophoretic lanes. Reading from the bottom to the top of the first reaction product lane identifies the first four members of the first set of target nucleotide residues. Similarly, reading from the bottom to the top for the second and third reaction products provides the identification of the first four members of the second and third set of target nucleotide residues. To read the contiguous sequence, one reads from left to right and bottom to top to provide the sequence identified below the electrophoretic gel which corresponds exactly to the nucleotide sequence set forth in FIG. 2.

Of course, each of the reaction products in FIG. 3, can be separately separated and the information thereafter integrated. Moreover, the detection of label and separation can be performed simultaneously or sequentially. For example, when different flurophores are used to differentially label the sequencing nucleotide residue, the various reaction products can be simultaneously separated and detected using for example an Applied BioSystems, Inc. Gene Sequencer Model 373.

In a variation of the above sequencing methodology, the nucleic acid template is contained within a replicable vector such as a plasmid or phage. In such applications, the nucleic acid template generally comprises a fragment of nucleic acid obtained by restriction endonuclease digestion that is cloned into appropriate restriction site in the replicable vector. When so cloned, the primers used for primed template formation can be directed to a vector sequence which is adjacent to the inserted nucleic acid template. In this manner, the same primers can be used with a particular cloning vector while the nucleic acid template inserted into it is varied. Moreover, since an insert in a replicable vector contains adjacent vector sequences at both ends of the insert, sequencing can be primed from each of the adjacent vector sequences. Thus, if extension oligonucleotides having a length of 8 nucleotide residues are used, the insert can be sequenced from the adjacent vector sequence into the insert for approximately 4 kb. However, using the same replicable vector containing the same nucleic acid template, ligation primers for the other adjacent vector sequence can be used to sequence in the other direction to sequence an additional 4 kb of nucleic acid sequence thus providing upward to 8 kb of sequence information from a single clone. Of course, in practice, it is desirable to have an overlap in the sequence determined as between the sequencing from each end to confirm that the entire sequence has been determined. Thus, the practical size of an insert that can be sequenced using extension oligonucleotides having 8 nucleotide residues is somewhat less, e.g., about 7.5 kb.

Figure 5:
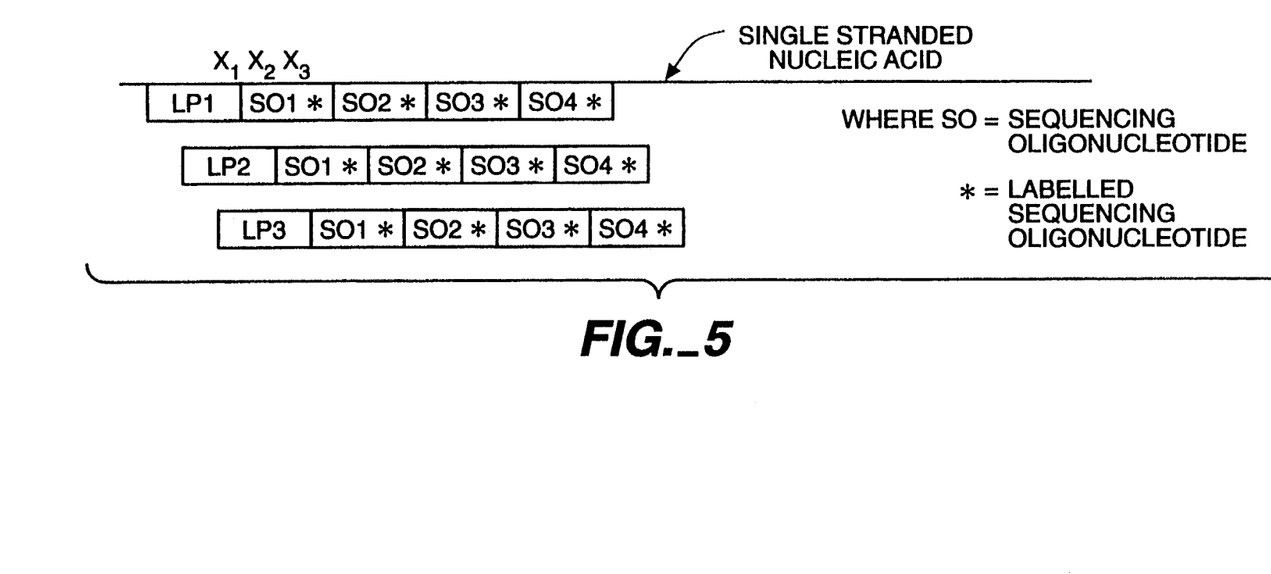
FIG. 5 depicts first, second and third ligation reaction products obtained in an alternate embodiment of the invention wherein each of the extension oligonucleotides used to form the ligation products shown contains a differentially labeled sequencing nucleotide residues at a predetermined nucleotide position in the extension oligonucleotides.

In an alternate embodiment, the labeled nucleotide residue is not contained within the terminating moiety but rather is contained within the extension oligonucleotide. When so used, the extension oligonucleotide is sometimes referred to as a sequencing oligonucleotide. When so used, the sequencing nucleotide residue is located at a predetermined nucleotide position in a manner analogous for that set forth in FIG. 4 for a terminating moiety. However, in this embodiment, the oligonucleotide does not contain a chain-terminating nucleotide. When such sequencing oligonucleotides are used as an extension oligonucleotide, the ligation product so formed contains one or more labeled nucleotide residues in each molecule of the ligation product formed. Further, since the sequencing nucleotide is located at a predetermined nucleotide position, each of the labeled sequencing nucleotide residues in the ligation product are separated by N-nucleotides. As with the previous embodiment, these labeled nucleotide residues are base paired with nucleotide residues in the nucleic acid template that comprise a set of target nucleotide residues defining a particular reading frame. As with the previous embodiment, the reading frame can be shifted by varying the terminal nucleotide residue in the ligation primer or the predetermined nucleotide position containing the labeled nucleotide residue. FIG. 5 sets forth the ligation product formed in this embodiment of the invention wherein the terminal nucleotide of the ligation primer is varied as between LP1, LP2 and LP3 and the labeled nucleotide is kept constant. In essence, the same sequence information is contained in each of the reaction products but is manifested in a different physical form. As such, the detection of the relative position of each of the labeled sequencing nucleotide residues and the label associated with each of those nucleotides is determined in a manner different from that of the previous embodiment.

Figure 6:
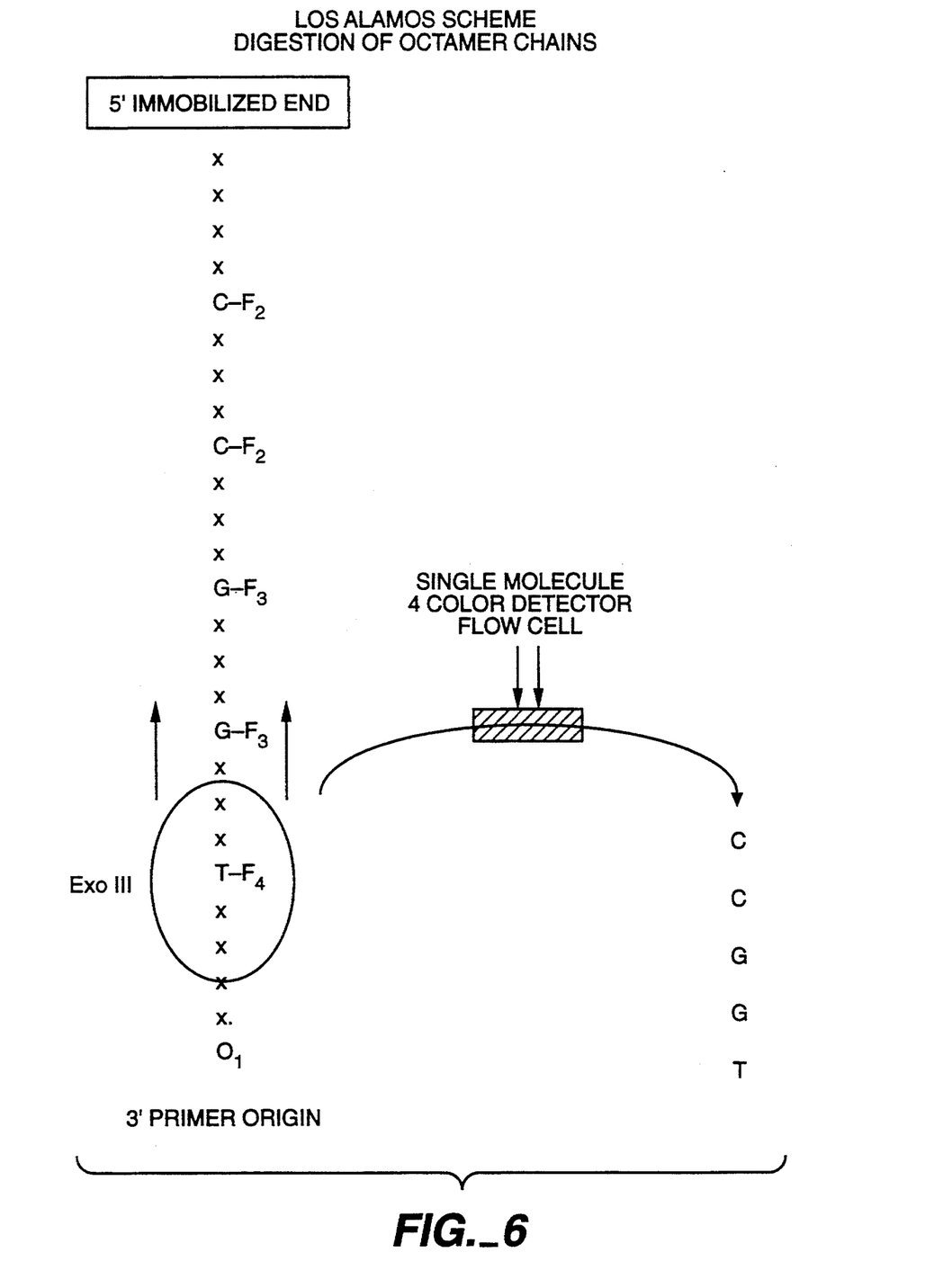
FIG. 6 depicts an alternate embodiment of the invention wherein an exonuclease and flow cell are used to detect labeled nucleotide residues in a ligation product.

In this regard, references is made to FIG. 6 which depicts a ligation product containing labeled nucleotide residues separated by an interval of four nucleotide residues. Label F2 is associated with cytosine nucleotide residues whereas label F3 is associate with guanidine nucleotide residues and label F4 is associated with thymidine nucleotide residues. As can be seen, the 5' end of the ligation product is immobilized. Such immobilization is readily obtained by utilizing a terminating moiety in the reaction mixture that contains one of the members of a binding pair covalently attached thereto. In this approach, it is preferred that the terminating moiety be added after the addition of sequencing oligonucleotide to the primed template so as to maximize the concentration and length of ligation product formed. After the covalent incorporation of the terminating moiety into the ligation product and denaturation, the labeled ligation product is contacted with a support containing the other member of the binding pair utilized in the terminating moiety. This provides not only for the separation of the labeled ligation product from the rest of the components of the reaction mixture but also allows for the determination of one or more of the nucleotide residues in a particular set of target nucleotides in the nucleic acid template.

In the case of single molecule sequencing, (See Keller, supra), the labeled positions in the ligation product have a defined offset relative to the ligation primer. Therefore, as shown in FIG. 6, each ligation product has the same sequence commencing at its 3' end. As a consequence, an exonuclease can be contacted with the immobilized ligation product such that the exonuclease digestion of the immobilized ligation product is synchronized. When coupled to an appropriate flow cell detector for the labels employed, the relative order and type of label contained in the ligation product can be determined and the sequence of the target nucleotides in the nucleic acid ascertained.

Having described the preferred embodiments of the invention, it will be apparent to those skilled in the art that various modifications can be made to the embodiments disclosed herein and that such modifications are intended to be within the scope of the appended claims.

What is claimed is:

1. A method comprising
   (a) contacting a nucleic acid template with a primer capable of hybridizing to said template to form a primed template;
   (b) contacting said primed template with a pool of random extension oligonucleotides having a length of N nucleotides where N is an integer from 4 to 9 wherein said extension oligonucleotides comprise random nucleotide positions containing any one of the nucleotides A. T, G or C and a predetermined nucleotide position consisting of one of the four different nucleotide residues A. T, G or C, each different nucleotide at said predetermined position containing a different nucleotide-specific label; and
   (c) covalently linking with a ligase (1) said primer to an extension oligonucleotide and (2) two or more extension oligonucleotides when any of said primer and extension oligonucleotides are adjacently hybridized to said nucleic acid template, wherein said covalent linking produces a reaction product comprising at least one ligation product hybridized to said nucleic acid template.

2. A method comprising
   (a) contacting a nucleic acid template with a primer capable of hybridizing to said template to form a primed template and
   (b) contacting said primed template with a pool of random extension oligonucleotides and termination moieties wherein said random extension oligonucleotides have a length of N nucleotides where N is an integer from 4 to 9 and containing any one of A, T, G or C residues at each nucleotide position and wherein said termination moieties comprise a chain-terminating terminal nucleotide and one of the four nucleotide residues A, T, G or C each containing a different nucleotide-specific label at a predetermined position in said termination moieties; and
   (c) covalently linking with a ligase: (1) said primer to an extension oligonucleotide or termination moiety, (2) two or more extension oligonucleotides and (3) an extension oligonucleotide and termination moiety when any of said primer, extension oligonucleotide or termination moiety are adjacently hybridized to said nucleic acid template, wherein said covalent linking produces a reaction product comprising at least one ligation product hybridized to said nucleic acid template and wherein said covalent linking is capable of being terminated by said chain-terminating terminal nucleotide in said termination moiety.

3. The method of claim 1 or 2 wherein said primer is blocked at either the 5' or 3' terminus so that extension is only in one direction and said reaction product comprises labeled ligation product containing one or more of said labeled nucleotide residues base paired with one or more members of a first set of target nucleotide residues in said nucleic acid template spaced at an interval of N nucleotides.

4. The method of claim 3 further comprising determining the nucleotide position and label of one or more labeled nucleotide residues in said labeled ligation product as an indication of the target nucleotide residue in said nucleic acid template with which said labeled nucleotide residue is base-paired.

5. The method of claim 3 further comprising the formation of second through $N^{th}$ reaction products wherein the labeled nucleotide residues in the second through $N^{th}$ labeled ligation products are base-paired respectively with one or more members of second through $N^{th}$ target nucleotide residues in said nucleic acid template, wherein the target nucleotide residues in each set are spaced at an interval of N nucleotides and each set is offset from one of the other sets by one nucleotide residue.

6. The method of claim 5 further comprising determining the nucleotide position and label of one or more labeled nucleotide residues in the labeled ligation products in said first through $N^{th}$ reaction products as an indication of the target nucleotide residues in said nucleic acid template with which said labeled nucleotide residues are base-paired.

7. The method of claim 6 wherein said nucleic acid template is contained within a replicable vector and first and second vector sequences adjacent to said template is known, said method comprising separately contacting first and second samples of said template each containing at least one of said adjacent vector sequences with primers P1 and P2, wherein said P1 primer is capable of hybridizing with said at least one adjacent vector sequence in said first sample and said P2 primer is capable of hybridizing with the other of said adjacent vector sequence in said second sample.

8. A method for determining the nucleotide sequence of one or more members of a set of target nucleotide residues in a nucleic acid spaced at an interval of N nucleotides where N is an integer from 4 to 9, said method comprising forming labeled ligation product hybridized to sample template of said nucleic acid, wherein said labeled ligation product comprises covalently linked sequence specific oligonucleotides having a length of N nucleotides covalently linked to each other in either a 5' to 3' or 3' to 5' direction and nucleotide-specific labels spaced at an interval of N nucleotides or multiple thereof and detecting said nucleotide-specific label in said ligation product as an indication of the nucleotide sequence of said set of target nucleotides.

9. The method of claim 8 wherein said labeled ligation product comprises a plurality of labeled ligation product having lengths that differ by N nucleotides wherein a particular nucleotide-specific label is associated with a ligation product having a particular length.

10. The method of claim 8 wherein a molecule of said labeled ligation product contains more than one nucleotide-specific label.

11. Composition comprising a pool of oligonucleotides having a length from 4 to 9 nucleotide residues and containing at a predetermined nucleotide position one of the four different nucleotide residues A, T, G or C, each residue containing a different nucleotide-specific label and random nucleotide positions containing any of the residues A, T, G or C at each of the other nucleotide positions.

12. The composition of claim 11 wherein said predetermined nucleotide position is not a terminal nucleotide position.

13. The composition of claim 12 wherein a terminal nucleotide position in said oligonucleotide comprises a chain-terminating nucleotide residue incapable of participating in enzyme-mediated ligation.

* * * * *

UNITED STATES PATENT AND TRADEMARK OFFICE
CERTIFICATE OF CORRECTION

PATENT NO. : 5,403,708

DATED : April 4, 1995

INVENTOR(S) : BRENNAN et al.

It is certified that error appears in the above-indentified patent and that said Letters Patent is hereby corrected as shown below:

Column 1, line 11, delete "chemical-degradation" and insert therefor --chemical degradation--.

Column 1, line 51, delete "Gene" and insert therefor --Gene--.

Claim 1, column 10, line 33, immediately following "nucleotides A" delete "." and insert therefor --,--.

Claim 1, column 10, line 35, immediately following "nucleotides A" delete "." and insert therefor --,--.

Claim 2, column 10, line 62, immediately following "ligase" delete ":".

Claim 9, column 12, line 22, delete "product" and insert therefor --products--.

Signed and Sealed this

Eighteenth Day of June, 1996

Attest:

BRUCE LEHMAN

*Attesting Officer*              *Commissioner of Patents and Trademarks*